US009254147B2

(12) United States Patent
Adams et al.

(10) Patent No.: US 9,254,147 B2
(45) Date of Patent: Feb. 9, 2016

(54) TRANS-URETHRAL SLING DELIVERY DEVICE

(71) Applicant: Empire Technology Development LLC, Wilmington, DE (US)

(72) Inventors: John Mathew Adams, Snohomish, WA (US); Daniel Hawkins, Bellevue, WA (US)

(73) Assignee: Empire Technology Development LLC, Wilmington, DE (US)

(*) Notice: Subject to any disclaimer, the term of this patent is extended or adjusted under 35 U.S.C. 154(b) by 130 days.

(21) Appl. No.: 14/112,037

(22) PCT Filed: Jan. 14, 2013

(86) PCT No.: PCT/US2013/021503
§ 371 (c)(1),
(2) Date: Oct. 16, 2013

(87) PCT Pub. No.: WO2014/109775
PCT Pub. Date: Jul. 17, 2014

(65) Prior Publication Data
US 2014/0200392 A1    Jul. 17, 2014

(51) Int. Cl.
*A61F 2/00* (2006.01)
*A61B 17/34* (2006.01)
*A61B 17/00* (2006.01)

(52) U.S. Cl.
CPC .......... *A61B 17/3468* (2013.01); *A61B 17/3421* (2013.01); *A61F 2/0045* (2013.01); *A61B 2017/00805* (2013.01)

(58) Field of Classification Search
CPC . A61B 17/3468; A61F 2/0045; A61F 2/0036; A61F 2/0004; A61F 2/0031

USPC ................................................ 600/29–32, 37
See application file for complete search history.

(56) References Cited

U.S. PATENT DOCUMENTS

| 7,364,541 B2 | 4/2008 | Chu et al. |
| 2006/0100640 A1 | 5/2006 | Bolduc |

(Continued)

FOREIGN PATENT DOCUMENTS

| EP | 1602336 B1 | 4/2012 |
| WO | 0033909 A1 | 6/2000 |

(Continued)

OTHER PUBLICATIONS

International Search Report for PCT/US2013/021503 filed Jan. 14, 2013, mailed on May 1, 2013.

(Continued)

*Primary Examiner* — John Lacyk
(74) *Attorney, Agent, or Firm* — Turk IP Law, LLC

(57) ABSTRACT

Technologies are generally provided for a trans-urethral sling delivery device for deploying a sub-urethral sling to support a urethra to treat urinary incontinence. A trocar and a delivery tube may be advanced through the urethra, and the trocar may puncture a hole in the urethral wall. The delivery tube may be configured to form a curved position such that a curved portion may extend from the hole in the urethral wall into an area surrounding the urethra near the bladder. A sub-urethral sling may be attached to a flexible delivery tool in a reduced delivery profile, and the flexible delivery tool with the attached sub-urethral sling may be advanced through the curved delivery tube. The delivery tube may be rotated to enable the delivery tool to anchor each end of the sub-urethral sling on each side of the urethra with a portion of the sling supporting the urethra from beneath.

15 Claims, 9 Drawing Sheets

(56) References Cited

U.S. PATENT DOCUMENTS

| | | |
|---|---|---|
| 2006/0217589 A1 | 9/2006 | Wan et al. |
| 2008/0132753 A1 | 6/2008 | Goddard |
| 2010/0130815 A1 | 5/2010 | Eliachar et al. |
| 2010/0274074 A1* | 10/2010 | Khamis et al. .................. 600/37 |
| 2012/0108895 A1 | 5/2012 | Neuman |
| 2012/0238803 A1 | 9/2012 | Lund |

FOREIGN PATENT DOCUMENTS

| | | |
|---|---|---|
| WO | 02071953 A2 | 9/2002 |
| WO | 02085188 A2 | 10/2002 |
| WO | 2005046511 A2 | 5/2005 |
| WO | 2005122954 A1 | 12/2005 |
| WO | 2009126476 A1 | 10/2009 |
| WO | 2010117700 A1 | 10/2010 |
| WO | 2011008167 A1 | 1/2011 |
| WO | 2011082350 A1 | 7/2011 |
| WO | 2012083159 A2 | 6/2012 |

OTHER PUBLICATIONS

Written Opinion of the International Searching Authority in the counterpart PCT International Patent Application No. PCT/US2013/021503, mailed May 1, 2013.

* cited by examiner

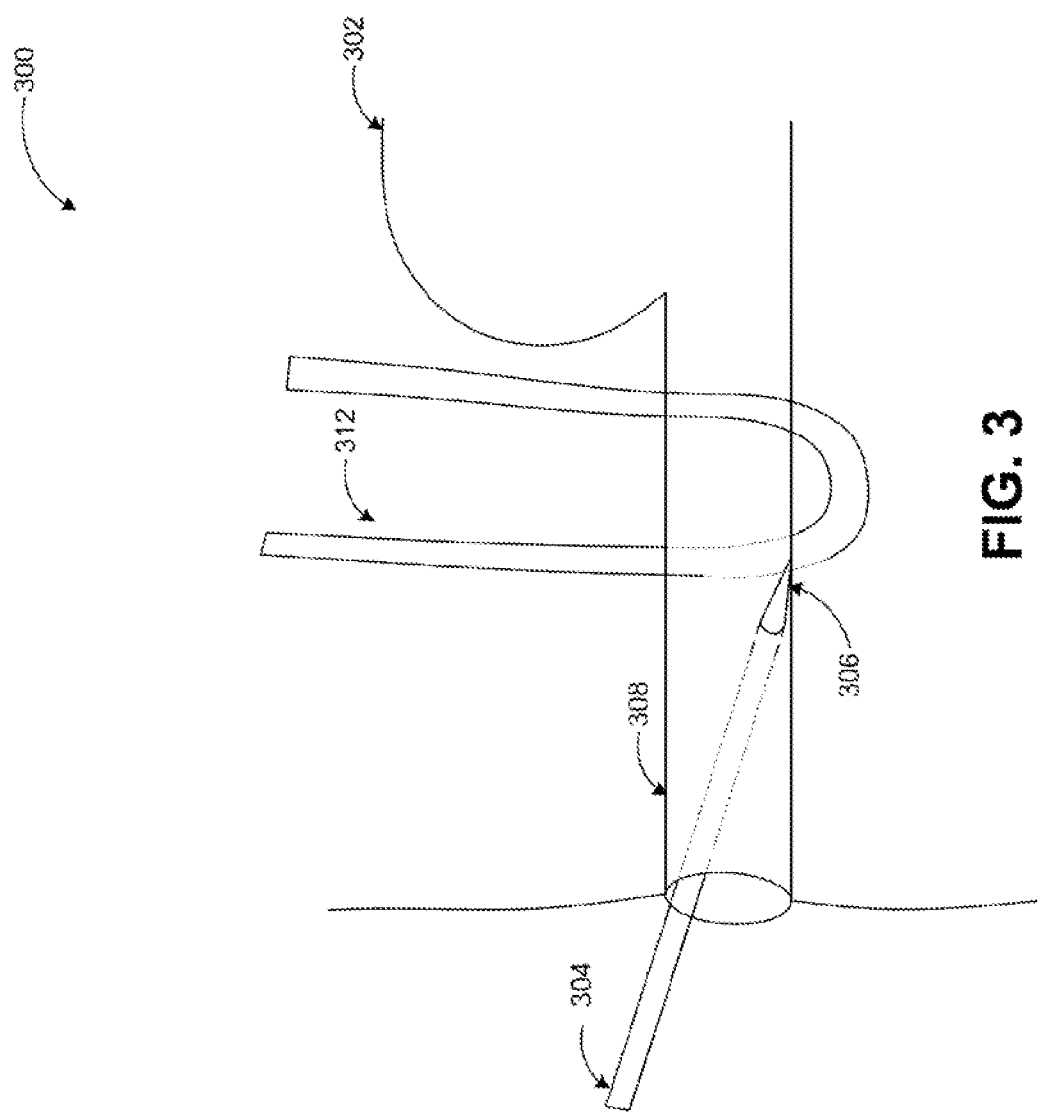

TRANS-URETHRAL SLING DELIVERY DEVICE

CROSS-REFERENCE TO RELATED APPLICATION

This Application is the U.S. National Stage filing under 35 U.S.C. §371 of PCT Application Ser. No. PCT/US2013/021503 filed on Jan. 14, 2013. The PCT application is hereby incorporated by reference in its entirety.

BACKGROUND

Unless otherwise indicated herein, the materials described in this section are not prior art to the claims in this application and are not admitted to be prior art by inclusion in this section.

Female urinary stress incontinence is a common ailment affecting more than 2 million women annually. Urinary control relies on the finely coordinated activities of the smooth muscle tissue of the urethra and bladder, skeletal muscle, voluntary inhibition, and the autonomic nervous system. Urinary stress incontinence can result from anatomic, physiologic, or pathologic (disease) factors due to aging and childbirth, and can eventually cause inadequate urinary storage or control which may result in bladder leakage. Some effective treatments for incontinence the surgical implantation of device called slings that provide mechanical support for the urethra when pelvic organs shift during points of stress including coughing, sneezing, and laughing, for example. Sling implantation generally involves small skin incisions as well as an incision through the upper vaginal wall to gain appropriate access to position the sling beneath the urethra. Some current sling insertion techniques involve using bulky delivery tools and/or sling containment devices, which can generate significant tissue separation and therefore bleeding to enable implantation. Additionally, the force required on the delivery tool to position the bulky sling devices may cause significant patient discomfort and may require anesthesia.

SUMMARY

The following summary is illustrative only and is not intended to be in any way limiting. In addition to the illustrative aspects, embodiments, and features described above, further aspects, embodiments, and features will become apparent by reference to the drawings and the following detailed description.

According to some examples, the present disclosure describes a trans-urethral delivery device for positioning a sub-urethral sling. The trans-urethral delivery device may include a trocar configured to puncture a wall of a urethra, a delivery tube configured to fit over the trocar and configured to be curved into a curved position, a sub-urethral sling configured in a reduced delivery profile for delivery through the delivery tube, and a flexible delivery tool configured to advance the sub-urethral sling through the delivery tube to deploy the sub-urethral sling in a position for supporting the urethra and anchoring the sub-urethral sling at the urethra.

According to other examples, the present disclosure describes a method for delivering a sub-urethral sling employing a trans-urethral delivery device. The method may include advancing a trocar through a urethra such that a lower interior wall of the urethra may be punctured, passing an delivery tube over the trocar through the punctured lower interior wall of the urethra, removing the trocar, curving the delivery tube into a curved position such that a curved portion of the delivery tube extends upwards from the puncture in the urethra, and attaching a portion of a sub-urethral sling configured in a reduced delivery profile at a distal end of a flexible delivery tool.

According to other examples, the present disclosure describes a method for delivering a sub-urethral sling employing a trans-urethral delivery device. The method may include advancing a trocar through a urethra to puncture a lower interior wall of the urethra, passing a delivery tube over the trocar through the punctured lower interior wall of the urethra, removing the trocar, curving the delivery tube into a curved position such that a curved portion of the delivery tube extends upwards from the puncture in the urethra, attaching a portion of a sub-urethral sling configured in a reduced delivery profile at a distal end of a flexible delivery tool, advancing the flexible delivery tool including the sub-urethral sling in the reduced delivery profile through the delivery tube, and deploying the sub-urethral sling for supporting the urethra by anchoring a first end of the sub-urethral sling on one of a left side and a right side of the urethra, positioning a middle portion of the sub-urethral sling underneath the urethra, and anchoring a second end of the sub-urethral sling on the other of the left side and the right side of the urethra.

According to further examples, the present disclosure describes a system for delivering a sub-urethral sling employing a trans-urethral delivery device. The system may include a trocar to puncture a lower interior wall of a urethra, a delivery tube configured to fit over the trocar and to be curved into a curved position such that a curved portion of the delivery tube extends upwards from the puncture in the lower interior wall of the urethra, a sub-urethral sling configured to be rolled into a reduced delivery profile for delivery through the delivery tube, and a flexible delivery tool configured to enable the sub-urethral sling to be attached to a distal end of the flexible delivery tool in the reduced delivery profile and to advance the sub-urethral sling through the delivery tube for deploying the sub-urethral sling in a position for supporting the urethra and anchoring the sub-urethral sling at the urethra.

According to yet other examples, the present disclosure describes a method of manufacturing a trans-urethral delivery device for delivery of a sub-urethral sling. The method may include providing a trocar to puncture a wall of a urethra, forming a delivery tube configured to fit over the trocar and to be curved into a curved position such that a curved portion of the delivery tube extends upwards from the puncture in the lower interior wall of the urethra, and forming a flexible delivery tool configured to advance the sub-urethral sling through the delivery tube for deploying and anchoring the sub-urethral sling in a position for supporting the urethra.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 3 illustrates an example trocar for puncturing a urethra and a trans-urethral delivery path for delivering a urethral sling;

DETAILED DESCRIPTION

Figure 1:
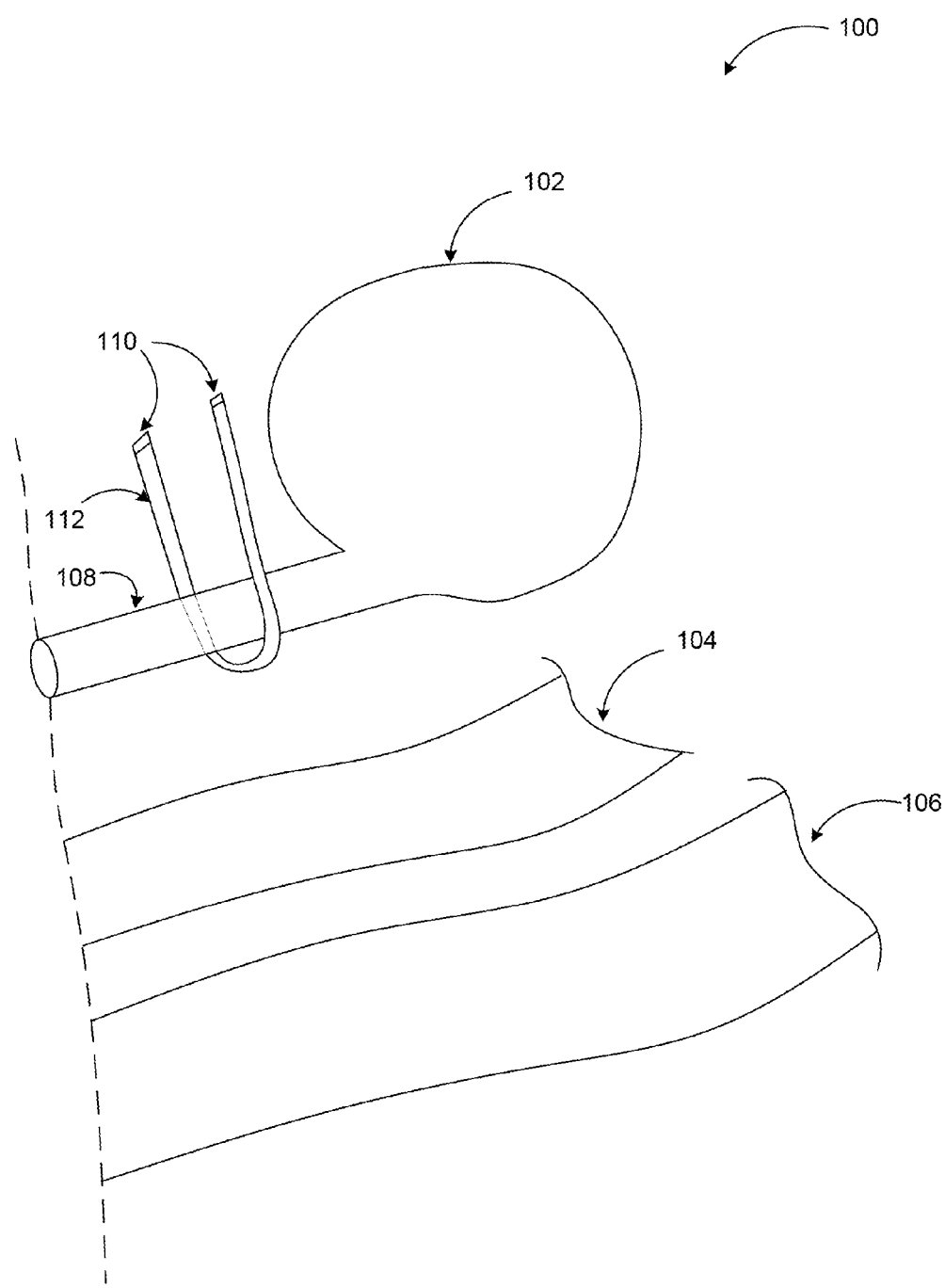
FIG. 1 illustrates an example anatomical layout of the pelvic cavity including the bladder, urethra, vagina, and colon.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

This disclosure is generally drawn, inter alia, to compositions, methods, apparatus, systems, devices, and/or computer program products related to providing a trans-urethral delivery device for positioning a sub-urethral sling.

Briefly stated, technologies are generally provided for a trans-urethral sling delivery device for deploying a sub-urethral sling to support a urethra to treat urinary incontinence. A trocar and a delivery tube may be advanced through the urethra, and the trocar may puncture a hole in the urethral wall. The delivery tube may be configured to form a curved position such that a curved portion may extend from the hole in the urethral wall into an area surrounding the urethra near the bladder. A sub-urethral sling may be attached to a flexible delivery tool in a reduced delivery profile, and the flexible delivery tool with the attached sub-urethral sling may be advanced through the curved delivery tube. The delivery tube may be rotated to enable the delivery tool to anchor each end of the sub-urethral sling on each side of the urethra with a portion of the sling supporting the urethra from beneath.

FIG. 1 illustrates an example anatomical layout of the pelvic cavity including the bladder, urethra, vagina, and colon, arranged in accordance with at least some embodiments as described herein. As illustrated in diagram 100, the basic pelvic anatomy of a female includes a bladder 102, a vagina 104, and a colon 106. The bladder 102 stores urine, and a urethra 108 is a short narrow tube connected to the bladder 102 that carries the urine from the bladder 102 out of the body. Some females may experience incontinence, which may be the inability to control leakage of bladder. A common solution for helping treat incontinence is the use of a sub-urethral sling 112.

In some embodiments, an example sub-urethral sling 112 may be an elongated mesh ribbon or tape, a middle portion of which may be positioned underneath the urethra 108 for supporting the urethra 108 from beneath. Each end 110 of the sub-urethral sling 112 may be anchored in position above and to either side of the urethra in soft tissue surrounding the bladder for holding the sub-urethral sling 112 in place for supporting the urethra 108 from beneath. When the ends 110 are anchored in the soft tissue, the middle portion of the sub-urethral sling 112 that extends between the two ends 110 may be underneath the urethra 108, and may provide support by holding up the urethra 108.

In an example embodiment, the ends 110 of the sub-urethral sling 112 may be positioned slightly posterior in relation to the middle portion of the sub-urethral sling 112, such that the middle portion of the sub-urethral sling 112 is positioned at an angle pointing towards the obturator foramen of the pelvic bone. In some example embodiments, the ends 110 of the sub-urethral sling 112 may be positioned through the obturator foramen. The obturator foramen is the hole created by the ischium and pubis bones of the pelvis through which nerves and muscles pass and is located posteriorly in relation to the urethra 108. The ends 110 may be passively or self-anchored in the soft tissue. For example, the ends 110 of the sub-urethral sling 112 may include barbs that enable the ends 110 to embed in the soft tissue naturally without requiring sutures. In other embodiments, the ends 110 may be anchored in place employing sutures or other similar anchoring techniques.

Figure 2:
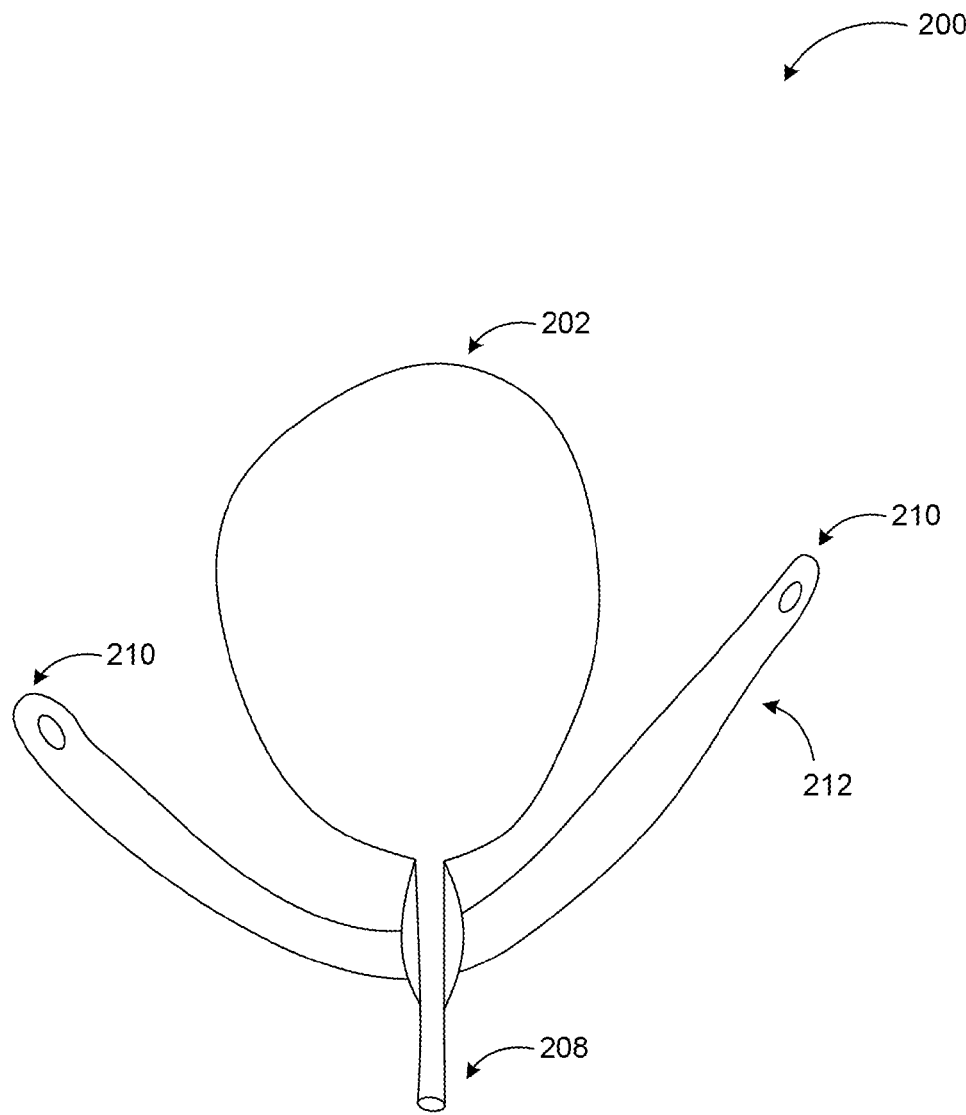
FIG. 2 illustrates an example urethral sling in position for supporting a urethra.

FIG. 2 illustrates an example urethral sling in position for supporting a urethra, arranged in accordance with at least some embodiments as described herein. As previously described, a sub-urethral sling 212 may be an elongated and substantially thin and flat mesh ribbon or tape. As illustrated in diagram 200, the sub-urethral sling 212 may deployed into an expanded position such that a middle portion of the sub-urethral sling 212 may be positioned underneath a urethra 208 for supporting the urethra 208 from beneath. Two ends 210 of the sub-urethral sling 122 may be positioned in the direction of and/or through the obturator foramen, such that the middle portion of the sub-urethral sling 212 is positioned an angle pointing towards the obturator foramen of the pelvic bone.

In a system according to embodiments, the sub-urethral sling 212 may be delivered and positioned employing minimally invasive surgery techniques in order to reduce risks, bleeding, recovery time, and pain for the patient. In order for the sub-urethral sling 212 to be inserted into the body and deployed to the expanded position, the sub-urethral sling 212 may be initially configured in a reduced delivery profile, or a more compact configuration, for enabling the sub-urethral sling 212 to be delivered through a minimally invasive technique. Once the sub-urethral sling 212 is delivered employing a minimally invasive technique as described herein, the sub-urethral sling 212 may be deployed into the expanded position such that the ends 210 may be anchored in a position in soft tissue surrounding the bladder 202 and urethra 208 for enabling the middle portion of the sub-urethral sling 212 to provide support to the urethra 208 from beneath.

FIG. 3 illustrates an example trocar for puncturing a urethra and a trans-urethral delivery path for delivering a urethral sling, arranged in accordance with at least some embodiments as described herein. As previously described, it may be desirable to insert and deploy a sub-urethral sling 312 in a position for supporting a urethra 308 employing a minimally invasive procedure. As illustrated in diagram 300, a trocar 304 may be inserted into the urethra. The trocar 304 may be a substantially long and straight rod having a sharply pointed distal end 306. The pointed distal end 306 of the trocar 304 may be configured to puncture a lower wall of the urethra 308 to provide access to the interior area of the pelvic area surrounding the urethra 308 and the bladder 302.

In some example embodiments the trocar 304 may be hollow for enabling passage of surgical tools through the hollow interior of the trocar 304. In other embodiments, the trocar 304 may be solid and may enable a tube to pass over the trocar 304. In yet other embodiments the trocar 304 may be coupled with a cannula, or delivery tube, such that the trocar 304 may be inside the cannula and inserted through the urethra 308 to puncture the urethral wall. After puncturing the wall of the urethra 308, the trocar 304 may be removed and the cannula may function as a portal for the subsequent insertion and placement of surgical tools and devices, such as the sub-urethral sling 312, which may be configured in an initial reduced delivery profile for insertion through the trocar 304 and/or cannula.

Figure 4A:
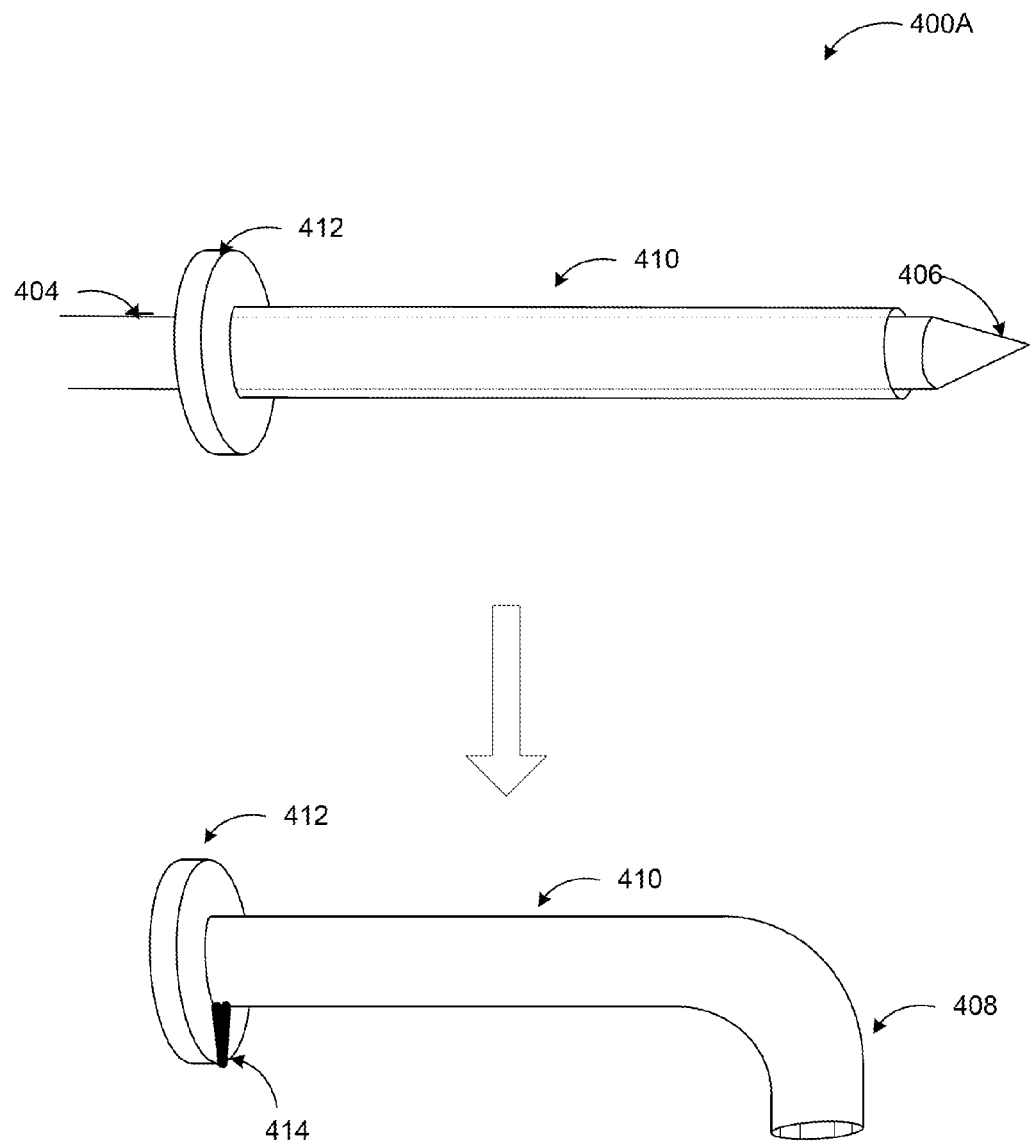
FIGS. 4A and 4B illustrate an example trocar including a delivery tube in straight and curved configurations.
Figure 4B:
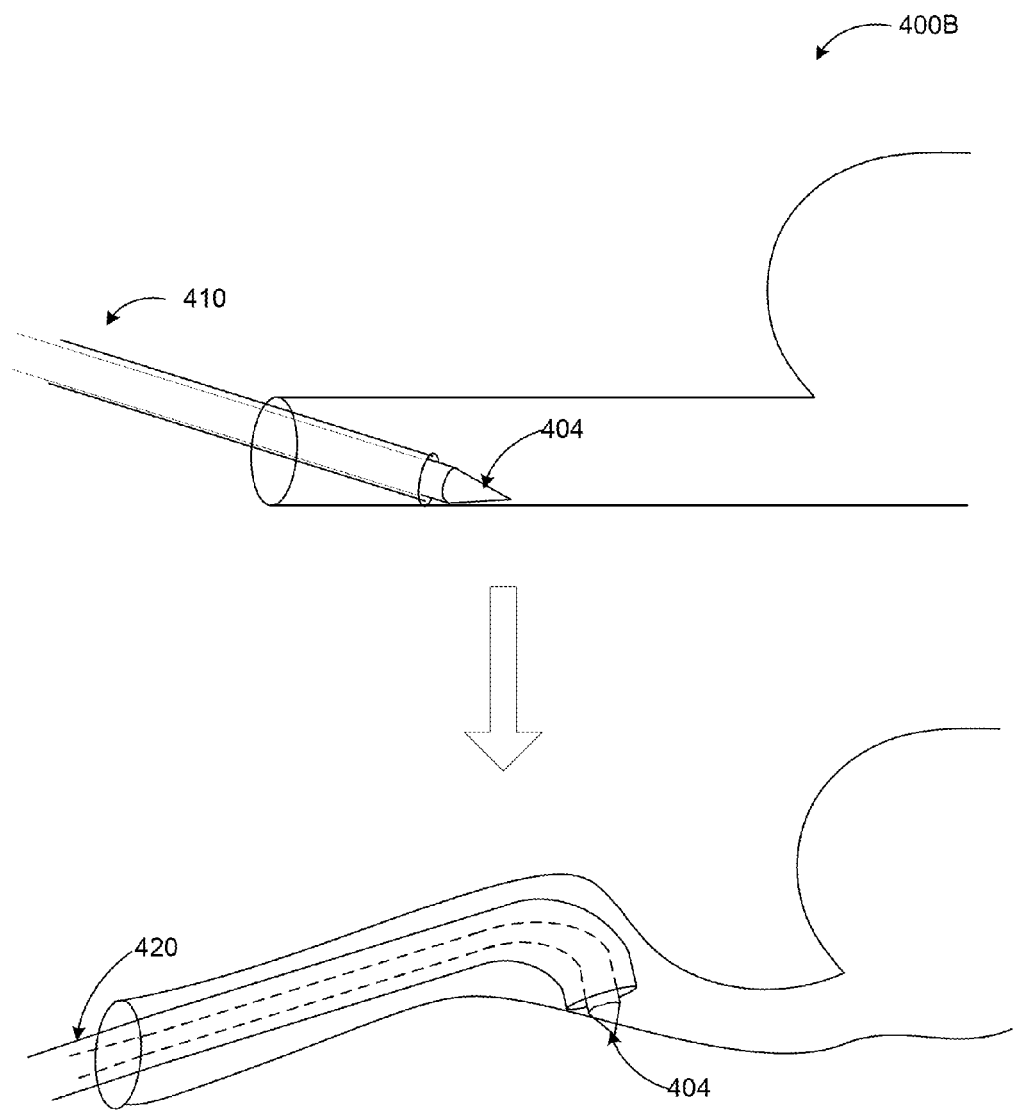

FIGS. 4A and 4B illustrates an example trocar including a delivery tube in straight and curved configurations, arranged in accordance with at least some embodiments as described herein. As illustrated in diagram 400A, a trocar 404 may be a substantially long and straight rod having a sharply pointed distal end 406 configured to puncture a lower wall of the urethra to provide access to an area surrounding the urethra near the bladder. The trocar may be coupled with a delivery tube 410, which may fit over the trocar 404. The delivery tube 410 may enable passage of surgical tools and the sub-urethral sling in a reduced delivery profile for insertion and deployment of the sub-urethral sling in a position to support the urethra.

In an example embodiment, the delivery tube 410 may be configured to slide over the trocar 404 in an initially straight position, and upon removal of the trocar 404, the delivery tube 410 may be configured to be curved into a curved position. For example, in an initial configuration, the delivery tube 410 may slide over the trocar 404 for insertion into the urethra. The trocar 404 may puncture a lower wall of the urethra, and the trocar 404 and the delivery tube 410 may advance into the interior area near the bladder outside of the urethra via the puncture in the urethral wall. The rigid structure of the trocar 404 may facilitate maintaining the delivery tube 410 in the straight position. An example rigid trocar 404 may be composed from a metal material such as stainless steel or nickel titanium alloy. Once the trocar 404 and the delivery tube 410 have advanced through the puncture in the urethral wall, the trocar 404 may be removed from the urethra such that only the delivery tube 410 may remain in position within the urethra with the distal tip of the delivery tube 410 extending from the puncture.

In a system according to embodiments, when the rigid trocar 404 is removed, the delivery tube 410 may be configured to curve into a curved position such that a curved portion 408 of the delivery tube 410 may extend at an angle from the puncture in the urethral wall into space surrounding the urethra. The curved portion 408 may be configured to extend at a range of angles from 0 degrees to 90 degrees with respect to the straight portion of the delivery tube 410. The delivery tube 410 may include a handle 412 portion on a proximal end, which may remain outside the body. The handle may enable the delivery tube 410 to be rotated from outside the body. The handle 412 may include a mark 414 which may indicate the direction of the curved portion 408 when inside the body.

In an example embodiment, the delivery tube 410 may be composed of a shape-memory material for enabling the delivery tube 410 to transition from the straight position to the curved position. An example shape-memory material may be a shape-memory polymer and/or a shape-memory metal. The shape-memory material may be configured in an initial permanent shape, manipulated into a deformed, or temporary shape, and then configured to return from the deformed, or temporary, shape to the original, or permanent, shape. The transition between the deformed and original shapes may be induced by an external stimulus. An example external stimulus may be a temperature change. For example, the shape-memory material may be configured to have a first shape at a first temperature and a second shape at a second temperature. The shape-memory material may also be configured to retain additional transitional shapes between the original shape and deformed shape. The transitions between each additional shape between the original shape and deformed shape may also be induced by an external stimulus, such as temperature change. In addition to temperature change, other external stimuli may trigger the transition between shapes, such as an electric field, magnetic field, light, and/or solution, as some examples. Example shape-memory metals and/or alloys may include spring stainless steel and nickel titanium alloy. Example shape-memory polymers may include polyurethanes, poly(styrene-butadiene) block copolymers, polynorbornenes, caprolactones, dioxanones, diol esters, ether-ester diols, carbonates, oligo(epsilon caprolactone)diol, lactic acid, lactide, glycolic acid, glycolide, oligo(p-dioxanone) diol, trimethylene carbonate, poly(styrene-butadiene)copolymers, oligo(epsilon caprolactone)diol/oligo(p-dioxanone)diol copolymers, and poly(epsilon-caprolactone) dimethacrylate-poly(n-butyl acrylate) copolymers, as some examples.

In a system according to embodiments, the delivery tube 410 may be composed of a shape-memory material that may be triggered to transition between permanent and deformed states by a temperature change. The delivery tube 410 may be formed such that an original shape of the delivery tube 410 may be a desired curved position. Before insertion into the urethra, the delivery tube 410 may be deformed into the straight position for advancing the delivery tube 410 over the trocar 404 and into the urethra. The delivery tube 410 may be deformed employing a temperature change, such as heating or cooling the shape-memory material to a temperature for enabling the delivery tube 410 to assume the desired deformed position.

The delivery tube 410 in the deformed shape may be slid over the trocar 404 and may be advanced through the urethra and through the puncture in the urethra into the interior space surrounding the urethra. The trocar 404 may be removed, and the delivery tube 410 may be naturally exposed to the internal body temperature of the individual. The internal body temperature may cause the delivery tube 410 to revert from the deformed shape, or the straight position, to the original curved position such that the curved portion of the delivery tube 410 may extend at an angle from the puncture in the urethra. The delivery tube 410 may be configured to return to the deformed shape, or straight position, in response to an additional temperature change, which may be applied to heat or cool the delivery tube 410 to a temperature for forming the deformed shape. Additionally, the delivery tube 410 may be formed from a flexible material, such that the trocar 404 may be re-inserted through the delivery tube 410 to cause the delivery tube 410 to re-form the straight position for subsequent removal from the urethra.

In another example embodiment, as illustrated in diagram 400B, a rigid straight delivery tube 410 may be initially advanced through the urethra. A flexible trocar 404 may be advanced through the rigid delivery tube 410, and the flexible trocar 404 may puncture the urethral wall. After the flexible trocar 404 has punctured the urethral wall, the rigid delivery tube 410 may be removed from the urethra leaving the flexible trocar 404 in place as a guide. A rigid curved delivery tube 420 may be advanced over the flexible trocar 404 through the urethra. The urethra is also a flexible tube, and the urethra may passively bend around the rigid curved delivery tube 420 as the curved delivery tube 420 advances through the urethra. The curved delivery tube 420 may be advanced through the puncture in the urethral wall into a position for enabling the sub-urethral sling to be deployed through the curved delivery tube 420.

Figure 5:
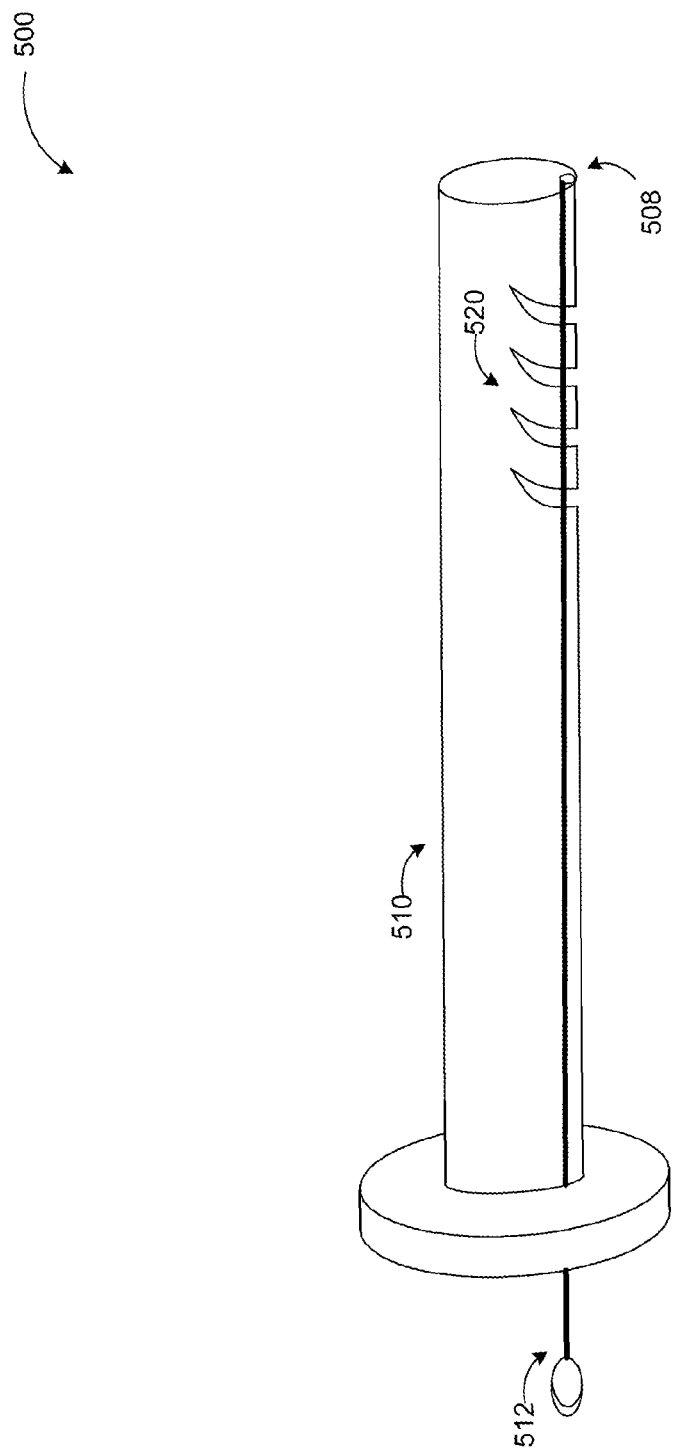
FIG. 5 illustrates an example delivery tube and cable for manually curving the delivery tube.

FIG. 5 illustrates an example delivery tube and cable for manually curving the delivery tube, arranged in accordance with at least some embodiments as described herein. As illustrated in diagram 500, the delivery tube 510 may be composed from a flexible material, such as a flexible metal and/or a flexible polymer material. When the delivery tube 510 is composed from a flexible material, the delivery tube 510 may be configured to be manually curved into a curved position with a curved portion extending from the puncture in the urethra. In order to manually curve the delivery tube 510, a cable 512 may be attached to the distal end 508 of the delivery tube 510, and a portion of the cable 512 may extend outside of a proximal end of the delivery tube 510 outside of the urethra and the body. A plurality of openings, or slits 520, may be formed near the distal end 508 of the delivery tube to facilitate curving the delivery tube to cause a curved portion to extend from the puncture in the urethra. In an example embodiment, the cable 512 may be tensioned in order to cause the distal end 508 of the delivery tube 510 to curve into the curved position. The cable 512 may be released to cause the delivery tube 510 to re-form the straight position for removal from the urethra.

Figure 6:
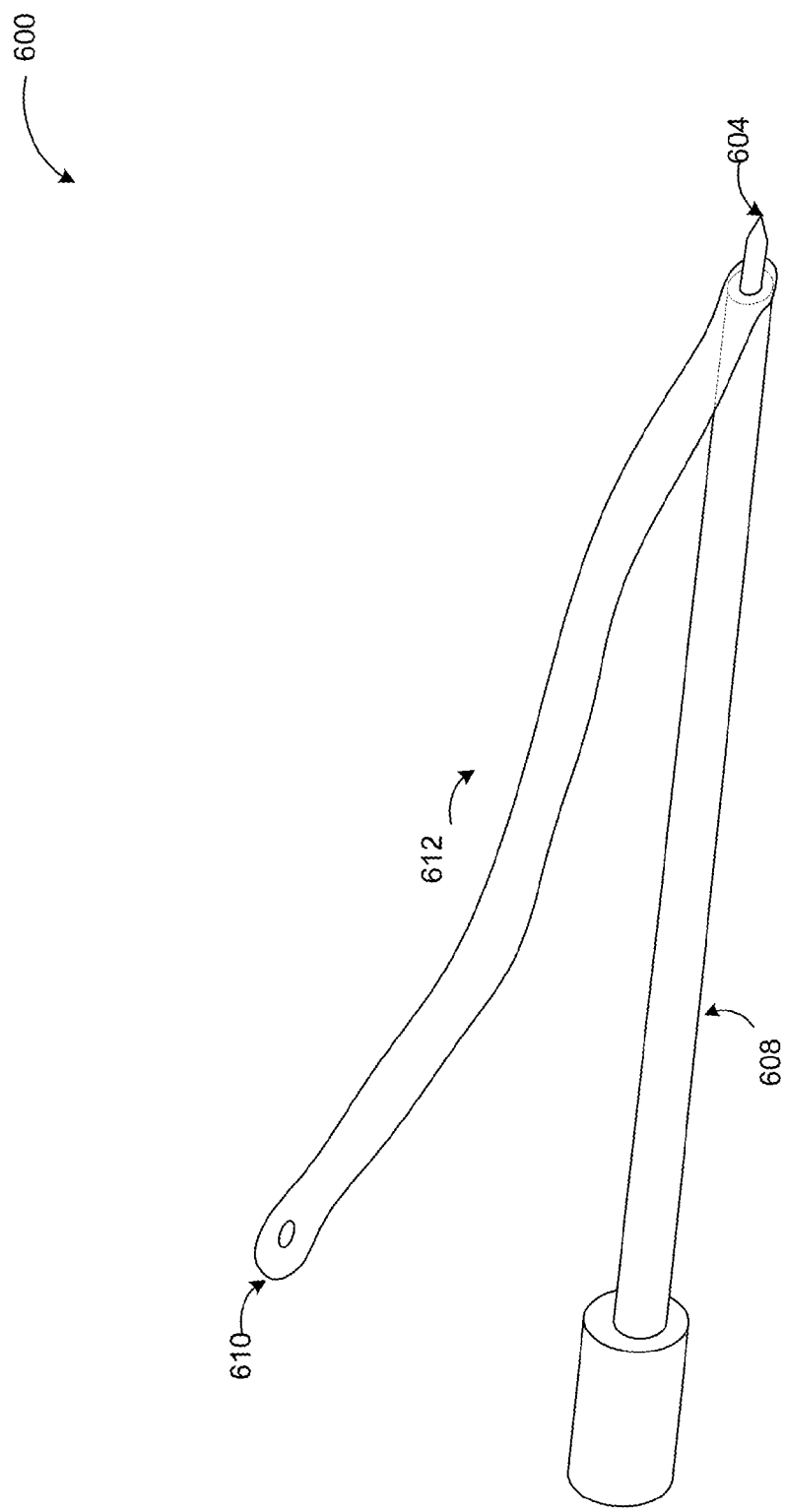
FIG. 6 illustrates attachment of a urethral sling to a flexible delivery tool.

FIG. 6 illustrates attachment of a urethral sling to a delivery tool, arranged in accordance with at least some embodiments as described herein. As illustrated in diagram 600, a sub-urethral sling 612 may be attached to a flexible delivery tool 608 for inserting the sub-urethral sling 612 and positioning the sub-urethral sling 612 employing a minimally invasive technique. In an example embodiment, the sub-urethral sling 612 may be an elongated mesh ribbon or tape with a size in a range configured to fit inside a delivery tube for insertion into the urethra. For example, the sub-urethral sling 612 may have a width in a range from about 1-2 cm.

In an example embodiment, the sub-urethral sling 612 may be configured to be attached to a distal 604 of the flexible delivery tool 608 through a hole, for example, or other similar releasable attachment that may be included on each end of the sub-urethral sling 612. Additionally, the sub-urethral sling 612 may be wrapped around the flexible delivery tool 608 for causing a reduced delivery profile, such that the sub-urethral sling 612 and the flexible delivery tool 608 may be able to fit within the interior of a delivery tube. The flexible delivery tool 608 with the attached sub-urethral sling 612 may be advanced through the delivery tube, which may be inserted into the urethra and through a puncture created in the urethra, as previously described. The flexible delivery tool 608 may be configured to enable delivery and positioning of the attached end of the sub-urethral sling 612 to a desired position in tissue near the urethra and the bladder. After anchoring the attached end of the sub-urethral sling 612, the flexible delivery tool 608 may be removed, and the other end 610 of the sub-urethral sling 612 may be attached to the flexible delivery tool 608 for subsequent insertion and positioning.

Figure 7:
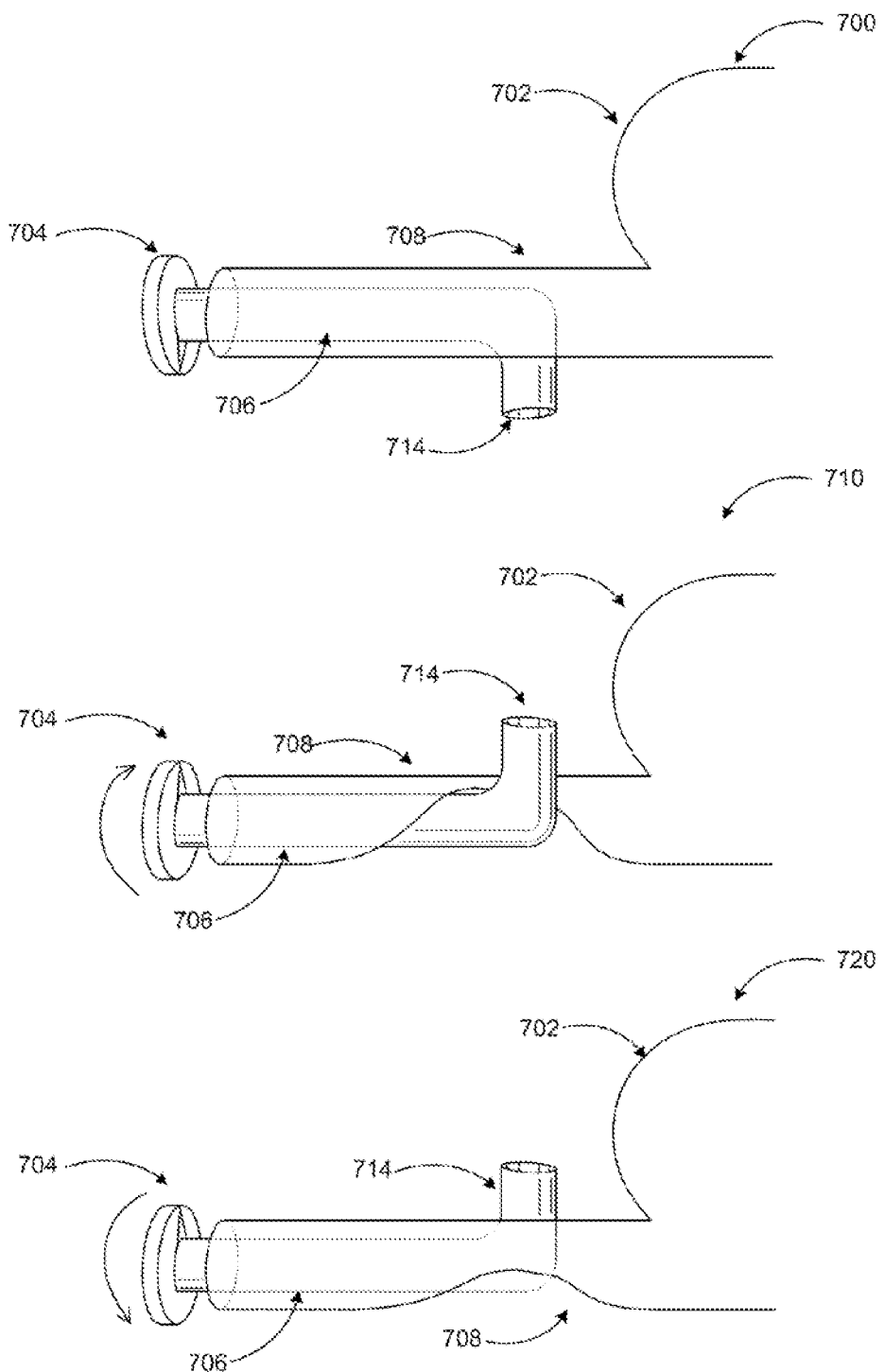
FIG. 7 illustrates rotation of a delivery tube for positioning a urethral sling on both sides of a urethra.

FIG. 7 illustrates rotation of a delivery tube for positioning a urethral sling on both sides of a urethra, arranged in accordance with at least some embodiments as described herein. As previously described, a rigid trocar and a delivery tube 706 may be inserted into the urethra, and a pointed end of the rigid trocar may puncture the urethral wall, such that the trocar and the delivery tube may advance through the puncture into a space surrounding the urethra and near the bladder 702. When the trocar is removed, the delivery tube 706 may be configured to curve into a curved position such that a curved portion 714 of the delivery tube 706 may extend at an angle from the puncture in the wall of the urethra 708 into the space surrounding the urethra 708. The curved portion 714 may be configured to extend at a range of angles from 0 degrees to 90 degrees with respect to the straight portion of the delivery tube 706.

Additionally, as illustrated in diagram 700, the delivery tube 706 may include a handle 704 on a proximal end, which may remain outside the body. The handle 704 may enable a physician to move and rotate the delivery tube 706 while it is inside the urethra 708. For example, as illustrated in diagrams 710 and 720, once the curved portion has extended from the puncture in the urethra 708, the delivery tube may be rotated for enabling the curved portion 714 to extend upwards to a right side and a left side of the urethra 708. The handle 704 may include a mark which may indicate the direction of the curved portion 714 when inside the body.

Figure 8:
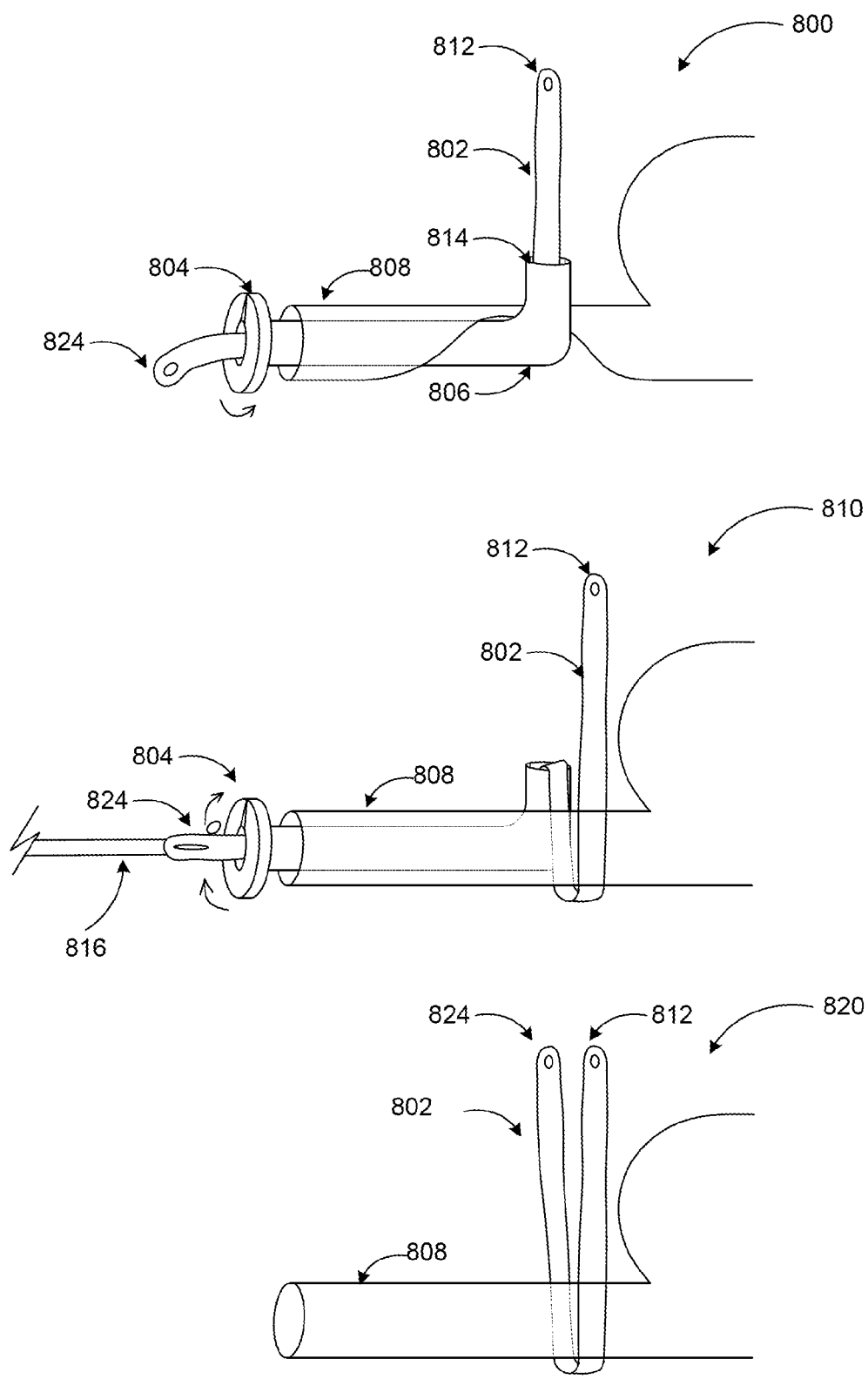
FIG. 8 illustrates placement of a urethral sling on both sides of a urethra, all arranged in accordance with at least some embodiments as described herein.

FIG. 8 illustrates placement of a urethral sling on both sides of a urethra, arranged in accordance with at least some embodiments as described herein. As previously described, once the delivery tube 806 has been advanced through the puncture in the urethra 808, a curved portion 814 of the delivery tube 806 may extend into space surrounding the urethra and near the bladder from the puncture in the urethra 808. A handle 804 attached to a proximal end of the delivery tube 806 may remain outside of the body and may enable the delivery tube 806 to be rotated to extend upwards to a right side and a left side of the urethra 808.

In an example embodiment, as illustrated in diagram 800, a sub-urethral sling 802 may be inserted into the urethra 808 and positioned in a position for supporting the urethra 808 employing the delivery tube 806 and a flexible delivery tool 816. In an example scenario for inserting the sub-urethral sling 802, once the delivery tube 806 has been advanced through the puncture in the urethra 808, and the curved portion 814 of the delivery tube 806 has been configured to extend from the puncture, the delivery tube 806 may be rotated to extend upwards and to one of the right and the left side of the urethra 808. A first end 812 of the sub-urethral sling 802 may be attached to the flexible delivery tool 816 as previously described in conjunction with FIG. 7, and the flexible delivery tool 816 along with the attached sub-urethral sling 802 may be advanced through the delivery tube 806. The flexible delivery tool 816 may deliver the attached first end 812 of the sub-urethral sling 802 to a desired position near the urethra and the bladder, and may anchor the first end 812 in place. The flexible delivery tool 816 may then be removed from the delivery tube 806 and the urethra 808.

Subsequently, as illustrated in diagram 810, a second end 824 of the sub-urethral sling 802 may be attached to the flexible delivery tool 816. The delivery tube 806 may be rotated to the other of the right side and left side of the urethra 808 employing the handle 804. The flexible delivery tool 816 including the attached second end 824 of the sub-urethral sling 802 may be advanced through the delivery tube 806, and the second end 824 of the sub-urethral sling may be delivered and anchored in soft tissue in a desired position on the other of the right and left side of the urethra 808. After both ends of the sub-urethral sling 802 have been delivered and positioned in soft tissue in a desired position near the urethra 808 and the bladder, the flexible delivery tool 816 and the delivery tube 806 may be removed from the urethra.

As illustrated in diagram 820, when the first end 812 and the second end 824 are anchored in position for supporting the urethra 808, the first end 812 may be anchored in soft tissue on one of a left side and a right side of the urethra and the second end may be anchored in soft tissue on the other of the left side and the right side of the urethra 808. The middle portion of the sub-urethral sling 802, which extends the first end 812 and the second end 824 of the sub-urethral sling 802 may be positioned underneath the urethra 808, such that the sub-urethral sling 802 is configured to provide support to the urethra 808 from beneath. While embodiments have been discussed above using specific examples, components, and configurations, they are intended to provide a general guideline to be used for a trans-urethral sling delivery device for deploying a sub-urethral sling to support a urethra to treat urinary incontinence. These examples do not constitute a limitation on the embodiments, which may be implemented using other components, modules, and configurations using the principles described herein. Furthermore, actions discussed above may be performed in various orders, especially in an interlaced fashion.

According to some examples, the present disclosure describes a trans-urethral delivery device for positioning a sub-urethral sling. The trans-urethral delivery device may include a trocar configured to puncture a wall of a urethra, a delivery tube configured to fit over the trocar and configured to be curved into a curved position, a sub-urethral sling configured in a reduced delivery profile for delivery through the delivery tube, and a flexible delivery tool configured to advance the sub-urethral sling through the delivery tube to deploy the sub-urethral sling in a position for supporting the urethra and anchoring the sub-urethral sling at the urethra.

According to some examples, the trocar may be configured to advance through the urethra and puncture through a lower inner wall of the urethra. The delivery tube may have a substantially circular cross sectional shape with a diameter in a range configured to fit over the trocar and enable passage of the flexible delivery tool and sub-urethral sling. The delivery tube may be configured to pass through the punctured urethra into an interior space near the urethra.

According to some examples, the delivery tube may be configured to curve into the curved position when the trocar may be removed such that a curved portion of the delivery tube extends upwards from the puncture in the urethra into the interior space near the urethra. The delivery tube includes a handle portion on a proximal end for enabling the curved portion of the delivery tube to be rotated to a left side and/or a right side of the urethra. The delivery tube may be composed from a shape-memory material and may have at least a first shape and a second shape with the first shape being a substantially straight position and the second being a substantially curved position.

According to some examples, the delivery tube may be configured to transition from the first shape to the second shape upon application of an external stimulus. The delivery tube may be configured to fit over the trocar when in the first shape and configured to extend upwards from the puncture in the urethra in the second shape. The shape-memory material may be one of: a shape-memory metal and/or a shape-memory polymer. The shape-memory polymer may be selected from one or more of: polyurethanes, poly(styrene-butadiene) block copolymers, polynorbornenes, caprolactones, dioxanones, diol esters, ether-ester diols, carbonates, oligo(epsilon caprolactone)diol, lactic acid, lactide, glycolic acid, glycolide, oligo(p-dioxanone)diol, trimethylene carbonate, poly(styrene-butadiene)copolymers, oligo(epsilon caprolactone)diol/oligo(p-dioxanone)diol copolymers, and poly(epsilon-caprolactone)dimethacrylate-poly(n-butyl acrylate) copolymers. The shape-memory metal may be selected from one or more of: spring stainless steel and nickel titanium alloy.

According to some examples, the trocar may be composed of a metal. The metal may be one of stainless steel or nickel titanium alloy. The delivery tube may be configured to be manually curved into the curved position. The delivery tube includes a cable attached at a distal end configured to be manually tensioned to manually curve the delivery tube into the curved position.

According to some examples, the sub-urethral sling may be configured to be wrapped around the flexible delivery tool in the reduced delivery profile. A first end and a second end of the sub-urethral sling may be configured to be attached to a distal end of the flexible delivery tool for enabling the flexible delivery tool to advance the sub-urethral sling through the delivery tube and to deploy the sub-urethral sling in position near the urethra. A first end of the sub-urethral sling may be anchored in soft tissue on one of a left side and a right side of the urethra, a middle portion extending between the first end and a second end of the sub-urethral sling may be positioned underneath the urethra, and the second end of the sub-urethral sling may be anchored in soft tissue on the other of the left side and the right side of the urethra, such that the sub-urethral sling supports the urethra from beneath.

According to other examples, the present disclosure describes a method for delivering a sub-urethral sling employing a trans-urethral delivery device. The method may include advancing a trocar through a urethra such that a lower interior wall of the urethra may be punctured, passing an delivery tube over the trocar through the punctured lower interior wall of the urethra, removing the trocar, curving the delivery tube into a curved position such that a curved portion of the delivery tube extends upwards from the puncture in the urethra, and attaching a portion of a sub-urethral sling configured in a reduced delivery profile at a distal end of a flexible delivery tool.

According to some examples, the method may also include advancing the flexible delivery tool including the sub-urethral sling in the reduced delivery profile through the delivery tube, and deploying the sub-urethral sling for supporting the urethra by anchoring a first end of the sub-urethral sling on one of a left side and a right side of the urethra, positioning a middle portion that extends between the first end and a second end of the sub-urethral sling underneath the urethra, and anchoring the second end of the sub-urethral sling on the other of the left side and the right side of the urethra.

According to some examples, the method may also include configuring the delivery tube to have a substantially circular cross sectional shape with a diameter in a range configured to fit over the trocar and enable passage of the flexible delivery tool and sub-urethral sling. The method may also include composing the delivery tube from a shape-memory material delivery tube such that the delivery tube may be configured to transition from a first shape to a second shape, wherein the first shape may be a substantially straight position to fit over the trocar and the second shape may be the curved position for enabling the curved portion to extend upwards from the puncture in the urethra when the trocar may be removed. The method may also include manually curving the delivery tube for extending the curved portion upwards from the puncture in the urethra. The method may also include manually curving the delivery tube by tensioning a cable attached to a distal end of the delivery tube.

According to some examples, the method may also include attaching a handle portion on a proximal end of the delivery tube for enabling the delivery tube to be rotated to a left side and a right side of the urethra. The method may also include including a mark on the handle portion for indicating a direction of the curved portion of the delivery tube.

According to some examples, the method may also include positioning the delivery tube in an initial position with the curved portion extending towards one of a right side and a left side of the urethra, advancing the flexible delivery tool with the attached sub-urethral sling through the delivery tube, anchoring a first end of the sub-urethral sling in soft tissue in a position above and on one of the right side and the left side of the urethra, rotating the delivery tube such that the curved portion extends towards the other of the right side and the left side of the urethra, and anchoring a second end of the sub-urethral sling in a position above and on the other of the right side and the left side of the urethra.

According to other examples, the present disclosure describes a method for delivering a sub-urethral sling employing a trans-urethral delivery device. The method may include advancing a trocar through a urethra to puncture a lower interior wall of the urethra, passing a delivery tube over the trocar through the punctured lower interior wall of the urethra, removing the trocar, curving the delivery tube into a curved position such that a curved portion of the delivery tube extends upwards from the puncture in the urethra, attaching a portion of a sub-urethral sling configured in a reduced delivery profile at a distal end of a flexible delivery tool, advancing the flexible delivery tool including the sub-urethral sling in the reduced delivery profile through the delivery tube, and deploying the sub-urethral sling for supporting the urethra by anchoring a first end of the sub-urethral sling on one of a left side and a right side of the urethra, positioning a middle portion of the sub-urethral sling underneath the urethra, and anchoring a second end of the sub-urethral sling on the other of the left side and the right side of the urethra.

The method may also include configuring the delivery tube to have a substantially circular cross sectional shape with a diameter in a range configured to fit over the trocar and enable passage of the flexible delivery tool and sub-urethral sling. The method may also include enabling the delivery tube to curve into the curved position when the trocar may be removed. The method may also include manually curving the delivery tube for extending a portion upwards from the puncture in the urethra. The method may also include manually curving the delivery tube by tensioning a cable attached to a distal end of the delivery tube.

According to other examples, the method may also include attaching a handle portion on a proximal end of the delivery tube for enabling the delivery tube to be rotated to the left side and the right side of the urethra. The method may also include including a mark on the handle portion for indicating a direction of the curved portion of the delivery tube. The method may also include positioning the delivery tube in an initial position with the curved portion extending towards one of the right side and the left side of the urethra, advancing the flexible delivery tool with the sub-urethral sling attached to the flexible delivery tool in the reduced delivery profile through the delivery tube, anchoring the first end of the sub-urethral sling in soft tissue in a position above and on one of the right side and the left side of the urethra, rotating the delivery tube such that the curved portion extends towards the other of the right side and the left side of the urethra, and anchoring the second end of the sub-urethral sling in a position above and on the other of the right side and the left side of the urethra.

According to further examples, the present disclosure describes a system for delivering a sub-urethral sling employing a trans-urethral delivery device. The system may include a trocar to puncture a lower interior wall of a urethra, a delivery tube configured to fit over the trocar and to be curved into a curved position such that a curved portion of the delivery tube extends upwards from the puncture in the lower interior wall of the urethra, a sub-urethral sling configured to be rolled into a reduced delivery profile for delivery through the delivery tube, and a flexible delivery tool configured to enable the sub-urethral sling to be attached to a distal end of the flexible delivery tool in the reduced delivery profile and to advance the sub-urethral sling through the delivery tube for deploying the sub-urethral sling in a position for supporting the urethra and anchoring the sub-urethral sling at the urethra.

According to some examples, at least one end of the sub-urethral sling may be configured to be attached to the flexible delivery tool. The sub-urethral sling may be deployed in the position for supporting the urethra by anchoring a first end of the sub-urethral sling on one of the right side and the left side of the urethra, positioning a middle portion extending between the first end and a second end of the sub-urethral sling underneath the urethra, and anchoring the second end of the sub-urethral sling on the other of the right side and the left side of the urethra.

According to some examples, the delivery tube includes a handle portion on a proximal end for enabling the delivery tube to be rotated to the left side and the right side of the urethra. The delivery tube includes a mark on the handle portion for indicating a direction of the curved portion of the delivery tube. The delivery tube may be positioned in an initial position with the curved portion extending towards one of the right side and the left side of the urethra for anchoring the first end of the sub-urethral sling in soft tissue in a position above and on one of the right side and the left side of the urethra.

According to some examples, the delivery tube may be rotated such that the curved portion extends towards the other of the right side and the left side of the urethra for anchoring the second end of the sub-urethral sling in a position above and on the other of the right side and the left side of the urethra. The delivery tube may be composed of a memory material to enable the delivery tube to automatically form the curved position when the trocar may be removed.

According to yet other examples, the present disclosure describes a method of manufacturing a trans-urethral delivery device for delivery of a sub-urethral sling. The method may include providing a trocar to puncture a wall of a urethra, forming a delivery tube configured to fit over the trocar and to be curved into a curved position such that a curved portion of the delivery tube extends upwards from the puncture in the lower interior wall of the urethra, and forming a flexible delivery tool configured to advance the sub-urethral sling through the delivery tube for deploying and anchoring the sub-urethral sling in a position for supporting the urethra.

According to some examples, the method may include configuring the delivery tube to have a substantially circular cross sectional shape with a diameter in a range configured to fit over the trocar and enable passage of the flexible delivery tool and sub-urethral sling. The method may include composing the delivery tube from a shape-memory material such that the delivery tube may be configured to transition from a first shape to a second shape, wherein the first shape may be a substantially straight position to fit over the trocar and the second shape may be the curved position for enabling the curved portion to extend upwards from the puncture in the urethra when the trocar may be removed. The method may include composing the flexible delivery tool from one of: a shape-memory metal or a shape-memory polymer.

According to some examples, the method may include attaching a cable to a distal end of the delivery tube for manually curving the delivery tube by tensioning the cable. The method may include attaching a handle portion on a proximal end of the delivery tube for enabling the delivery tube to be rotated to a left side and a right side of the urethra. The method may include including a mark on the handle portion for indicating a direction of a curved portion of the delivery tube.

According to some examples, the method may include composing the trocar from one of stainless steel or nickel titanium alloy. The method may include configuring a first end and a second end of the sub-urethral sling to be attached to a distal end of the flexible delivery tool for enabling the flexible delivery tool to advance the sub-urethral sling through the delivery tube and to deploy the sub-urethral sling in position near the urethra The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically connectable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A trans-urethral delivery device for positioning a sub-urethral sling, the trans-urethral delivery device comprising:
   a trocar configured to puncture a lower interior wall of a urethra;
   a delivery tube that includes a cable attached at a distal end and openings placed near the distal end of the delivery tube, wherein the delivery tube is configured to fit over the trocar to pass through the punctured lower interior wall of the urethra and is configured to curve into a curved position after removal of the trocar such that a curved portion of the delivery tube extends upwards from the puncture in the urethra and is enabled to be rotated to a left side and/or a right side of the urethra, wherein the curved position of the delivery tube is facilitated by the openings;
   a sub-urethral sling configured in a reduced delivery profile for delivery through the delivery tube; and
   a flexible delivery tool attached at the distal end to the sub-urethral sling in the reduced delivery profile, the flexible delivery tool configured to advance the sub-urethral sling through the delivery tube to deploy the sub-urethral sling in a position for supporting the urethra and anchoring the sub-urethral sling at the urethra.

2. The trans-urethral delivery device of claim 1, wherein the delivery tube has a substantially circular cross sectional shape with a diameter in a range configured to fit over the trocar and enable passage of the flexible delivery tool and sub-urethral sling.

3. The trans-urethral delivery device of claim 1, wherein the trocar is composed of a metal selected from one of: stainless steel or nickel titanium alloy.

4. The trans-urethral delivery device of claim 1, wherein the cable is configured to be manually tensioned to manually curve the delivery tube into the curved position.

5. The trans-urethral delivery device of claim 1, wherein the sub-urethral sling is configured to be wrapped around the flexible delivery tool in the reduced delivery profile.

6. The trans-urethral delivery device of claim 5, wherein a first end and a second end of the sub-urethral sling are configured to be attached to a distal end of the flexible delivery tool for enabling the flexible delivery tool to advance the sub-urethral sling through the delivery tube and to deploy the sub-urethral sling in position near the urethra.

7. The trans-urethral delivery device of claim 6, wherein a first end of the sub-urethral sling is anchored in soft tissue on one of a left side and a right side of the urethra, a middle portion extending between the first end and a second end of the sub-urethral sling is positioned underneath the urethra, and the second end of the sub-urethral sling is anchored in soft tissue on the other of the left side and the right side of the urethra, such that the sub-urethral sling supports the urethra from beneath.

8. A method for delivering a sub-urethral sling employing a trans-urethral delivery device, the method comprising:
   advancing a trocar through a urethra such that a lower interior wall of the urethra is punctured;
   passing a delivery tube over the trocar through the punctured lower interior wall of the urethra, wherein the delivery tube includes a cable attached at a distal end and openings near the distal end of the delivery tube;
   removing the trocar;
   curving the delivery tube into a curved position such that a curved portion of the delivery tube extends upwards from the puncture in the urethra, wherein the curved position is facilitated by the openings;
   attaching a portion of a sub-urethral sling configured in a reduced delivery profile at the distal end of a flexible delivery tool;
   advancing the flexible delivery tool including the sub-urethral sling in the reduced delivery profile through the delivery tube; and
   deploying the sub-urethral sling for supporting the urethra by anchoring a first end of the sub-urethral sling on one of a left side and a right side of the urethra, positioning a middle portion that extends between the first end and a second end of the sub-urethral sling underneath the urethra, and anchoring the second end of the sub-urethral sling on the other of the left side and the right side of the urethra.

9. The method of claim 8, further comprising:
   advancing a rigid straight delivery tube through the urethra;
   advancing a flexible trocar through the delivery tube to puncture a lower interior wall of the urethra;
   removing the rigid straight delivery tube from the urethra;
   advancing a rigid curved delivery tube over the flexible trocar through the urethra such that a curved portion of the rigid curved delivery tube extends upwards from the puncture in the urethra;
   removing the flexible trocar; and
   advancing the sub-urethral sling configured in a reduced delivery profile through the rigid curved delivery tube.

10. The method of claim 8, further comprising:
    attaching a handle portion on a proximal end of the delivery tube for enabling the delivery tube to be rotated to a left side and a right side of the urethra.

11. The method of claim 10, further comprising:
    including a mark on the handle portion for indicating a direction of the curved portion of the delivery tube.

12. The method of claim 11, further comprising:
    positioning the delivery tube in an initial position with the curved portion extending towards one of a right side and a left side of the urethra;
    advancing the flexible delivery tool with the attached sub-urethral sling through the delivery tube;
    anchoring the first end of the sub-urethral sling in soft tissue in a position above and on one of the right side and the left side of the urethra;
    rotating the delivery tube such that the curved portion extends towards the other of the right side and the left side of the urethra; and
    anchoring a second end of the sub-urethral sling in a position above and on the other of the right side and the left side of the urethra.

13. The method of claim 8, wherein the delivery tube includes a circular cross sectional shape, wherein the delivery tube includes a diameter that fits over the trocar to allow passage of the flexible delivery tool and sub-urethral sling.

14. The method of claim 8, further comprising:
    enabling the delivery tube to curve into the curved position when the trocar is removed.

15. The method of claim 8, further comprising:
    manually curving the delivery tube for extending a portion upwards from the puncture in the urethra by tensioning the cable attached to a distal end of the delivery tube.

* * * * *